US012059363B2

(12) United States Patent
Han

(10) Patent No.: US 12,059,363 B2
(45) Date of Patent: Aug. 13, 2024

(54) HYDRAULIC DAMPER AND INTELLIGENT PROSTHETICS

(71) Applicant: Shenzhen Mental Flow Technology Co., Ltd, Guangdong (CN)

(72) Inventor: Bicheng Han, Shenzhen (CN)

(73) Assignee: SHENZHEN MENTAL FLOW TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 18/452,028

(22) Filed: Aug. 18, 2023

(65) Prior Publication Data
US 2023/0390083 A1    Dec. 7, 2023

(30) Foreign Application Priority Data

Aug. 19, 2022  (CN) .......................... 202210996229.X

(51) Int. Cl.
*A61F 2/60* (2006.01)
*A61F 2/50* (2006.01)

(52) U.S. Cl.
CPC ........ *A61F 2/60* (2013.01); *A61F 2002/5006* (2013.01); *A61F 2002/5033* (2013.01); *A61F 2002/5072* (2013.01)

(58) Field of Classification Search
CPC ...... A61F 2/60; A61F 2/74; A61F 2/68; A61F 2/72; A61F 2002/5072; A61F 2002/5006;
(Continued)

(56) References Cited

U.S. PATENT DOCUMENTS

| 5,948,021 | A | 9/1999 | Radcliffe | |
|---|---|---|---|---|
| 6,613,097 | B1 * | 9/2003 | Cooper | A61F 2/68 |
| | | | | 623/44 |

(Continued)

FOREIGN PATENT DOCUMENTS

| CN | 1125976 A | 7/1996 |
|---|---|---|
| CN | 1714758 A | 1/2006 |

(Continued)

OTHER PUBLICATIONS

Chinese Patent No. CN 112460182 to Zhang et al published on Mar. 9, 2021.*

(Continued)

*Primary Examiner* — Pamela Rodriguez
(74) *Attorney, Agent, or Firm* — Maier & Maier, PLLC

(57) ABSTRACT

A hydraulic damper and an intelligent prosthetics. The hydraulic damper includes a housing, a piston, a piston rod, and a damping adjustment component; an energy storage chamber and a damping chamber loaded with hydraulic fluid are arranged inside the housing; the piston is movably provided in the damping chamber and separates the damping chamber into a first chamber and a second chamber, the energy storage chamber is closer to the second chamber; the piston rod is inserted into the first chamber, one end of the piston rod is connected to the piston, another end of the piston rod penetrates through one end of the housing away from the energy storage chamber; and the damping adjustment component is connected to the first chamber, the second chamber, and the energy storage chamber, respectively, to adjust resistance of movement of the piston, thereby reducing sealing difficulty and weight of the hydraulic damper.

18 Claims, 7 Drawing Sheets

(58) Field of Classification Search
CPC ... A61F 2002/5033; F16F 9/19; F16F 9/3207; F16F 9/44
See application file for complete search history.

(56) References Cited

U.S. PATENT DOCUMENTS

2016/0235558 A1    8/2016  Laurence et al.
2018/0098864 A1*  4/2018  Auberger .................. A61F 2/64

FOREIGN PATENT DOCUMENTS

| | | |
|---|---|---|
| CN | 102440854 A | 5/2012 |
| CN | 104154167 A | 11/2014 |
| CN | 105769395 A | 7/2016 |
| CN | 109996517 A | 7/2019 |
| CN | 111365306 A | 7/2020 |
| CN | 114081692 A | 2/2022 |
| CN | 114151493 A | 3/2022 |
| GB | 2343848 A * | 5/2000 |

OTHER PUBLICATIONS

Translation of Chinese Patent No. CN 111365306 obtained from website: https://worldwide.espacenet.com on Dec. 5, 2023.*
Translation of Chinese Patent No. CN 114151493 obtained from website: https://worldwide.espacenet.com on Dec. 5, 2023.*
Office Action issued on Sep. 9, 2022, in corresponding Chinese Patent Application No. 202210996229.X, 10 pages.
Office Action issued on Oct. 17, 2022, in corresponding Chinese Patent Application No. 202210996229.X, 5 pages.

* cited by examiner

HYDRAULIC DAMPER AND INTELLIGENT PROSTHETICS

CROSS-REFERENCE TO RELATED APPLICATIONS

This application claims priority to Chinese Patent Application No. 202210996229.X, filed on Aug. 19, 2022, the content of all of which is incorporated herein by reference.

FIELD

The present disclosure relates to the technical field of prosthetic products, in particular to a hydraulic damper and an intelligent prosthetics.

BACKGROUND

Prosthetics is a bionic product that allows amputees to stand and walk normally again. Currently, most of prosthetic products are hydraulic prosthetic products with good stability. Structure of a hydraulic damper in the hydraulic prosthetic products is usually composed of a cylindrical housing, an oil cylinder inside the cylindrical housing, an energy accumulator arranged inside the cylindrical housing, and a throttle valve device arranged outside the cylindrical housing; wherein a bottom end of a piston rod of the oil cylinder is inserted into the cylindrical housing and connected to a piston, while a top end of the piston rod extends out of the cylindrical housing. The piston divides an internal chamber of the oil cylinder into an upper chamber and a lower chamber, and the energy accumulator is located above the upper chamber, and the piston rod needs to penetrate through an energy storage chamber of the energy accumulator.

Due to the fact that the energy storage chamber stores high-pressure hydraulic oil to achieve energy accumulating, the requirements of the energy storage chamber for sealing-tightness are relatively high; while in the use of prosthetic products, the piston rod is a component that needs frequent upward and downward movement, and dynamic sealing treatment is needed between the piston rod and the energy storage chamber, resulting in a significant increase in the overall sealing difficulty of the hydraulic damper and an increase in production costs. Moreover, the piston rod needs to penetrate through the energy storage chamber to extend out of the cylindrical housing, and the length of the piston rod is long, making the weight of the hydraulic damper larger thereby increasing the burden on the user.

SUMMARY

The present disclosure provides a hydraulic damper, aiming to reduce the overall sealing difficulty and the weight of the hydraulic damper.

To achieve the above purpose, the hydraulic damper provided by the present disclosure is applied to prosthetics, and the hydraulic damper comprises:
 a housing, inside which an energy storage chamber and a damping chamber both loaded with a hydraulic fluid are arranged;
 a piston, movably arranged inside the damping chamber, separating the damping chamber into a first chamber and a second chamber, the energy storage chamber is closer to the second chamber;
 a piston rod, inserted into the first chamber, one end of the piston rod is connected to the piston, another end of the piston rod penetrates through one end of the housing away from the energy storage chamber; and
 a damping adjustment component, connected to the first chamber, the second chamber, and the energy storage chamber respectively, configured to adjust a resistance of a movement of the piston.

In some embodiments, the energy storage chamber, the second chamber, and the first chamber are sequentially distributed along an axial direction of the piston.

In some embodiments, the damping adjustment component comprises:
 a first throttle valve, one end of which is connected to the first chamber, and another end is connected to the energy storage chamber;
 a second throttle valve, one end of which is connected to the second chamber, and another end is connected to the energy storage chamber;
 a first non-return valve, through which the energy storage chamber is connected to the first chamber; and
 a second non-return valve, through which the energy storage chamber is connected to the second chamber.

In some embodiments, the hydraulic damper further comprises a first cylinder head and a second cylinder head arranged inside the housing, the damping chamber is formed between the first cylinder head and the second cylinder head, the first cylinder head is closer to the first chamber, the second cylinder head is closer to the second chamber;
 a liquid passage is arranged inside a side wall of the housing;
 an external circumferential wall of the first cylinder head is arranged with a slot that encloses with an inner wall of the housing to form a transit chamber, a first passage is arranged on the first cylinder head to be connected to both the first chamber and the transit chamber, the first non-return valve is arranged at one end of the first passage, the transit chamber is connected to the energy storage chamber through the liquid passage;
 a second passage is arranged on the second cylinder head to be connected to both the second chamber and the energy storage chamber, the second non-return valve is arranged at one end of the second chamber;
 the first throttle valve and the second throttle valve are arranged on an outer wall of the housing, two ends of the first throttle valve are respectively connected to the first chamber and the energy storage chamber correspondingly through the liquid passage, two ends of the second throttle valve are respectively connected to the second chamber and the energy storage chamber correspondingly through the liquid passage.

In some embodiments, an elastomer with a sealed chamber inside is arranged inside the energy storage chamber, In some embodiments, one end of the elastomer abuts against one end of the energy storage chamber away from the second chamber, and an external circumferential wall of the elastomer and an internal circumferential wall of the energy storage chamber are sealed and fitted together.

In some embodiments, one chamber wall of the energy storage chamber closer to the second chamber is arranged with a supporting part protrudingly toward the elastomer, and the supporting part abuts against the elastomer.

In some embodiments, the hydraulic damper further comprises an elastic device arranged in the second chamber, the elastic device acts elastically on the piston and applies a force on the piston toward the first chamber.

In some embodiments, the elastic device comprises a retractable spring, one end of the piston facing the second chamber is concavely arranged with a first locating slot, one end of the retractable spring is inserted into the first locating slot and elastically abuts against a bottom of the first locating slot;

one chamber wall of the second chamber closer to the energy storage chamber is concavely arranged with a second locating slot, another end of the retractable spring is inserted into the second locating slot and elastically abuts against a bottom of the second locating slot.

The present disclosure further provides an intelligent prosthetics comprising the above-mentioned hydraulic damper.

In the technical solution of the hydraulic damper of the present disclosure, the energy storage chamber is arranged closer to the second chamber, i.e. the energy storage chamber is arranged at one end of the housing away from the piston rod, so that the piston rod no longer needs to penetrate through the energy storage chamber and can extend out of the housing, which saves a dynamic sealing treatment between the piston rod and the energy storage chamber, reduces an overall sealing difficulty of the hydraulic damper and reduces production costs, and moreover saves a length of one segment of the piston rod passing through the energy storage chamber, reduces a length of the piston rod, and reduces a weight of the piston rod, thereby reducing an overall weight of the hydraulic damper, and making a weight of the prosthetics using the hydraulic damper lighter and more portable, thus reducing the burden on the user.

DETAILED DESCRIPTION OF EMBODIMENTS

Figure 1:
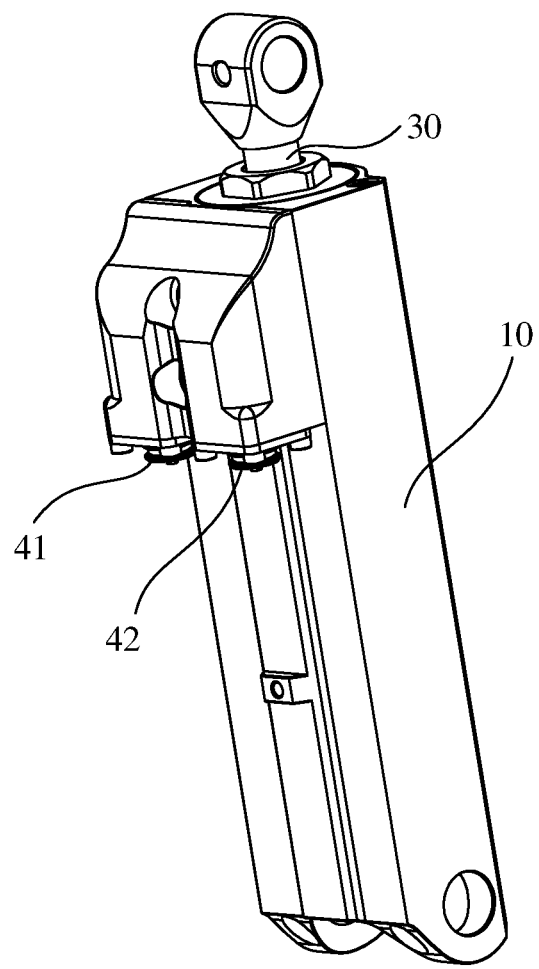
FIG. 1 is a schematic diagram of a structure of a hydraulic damper in one embodiment of the present disclosure.
Figure 2:
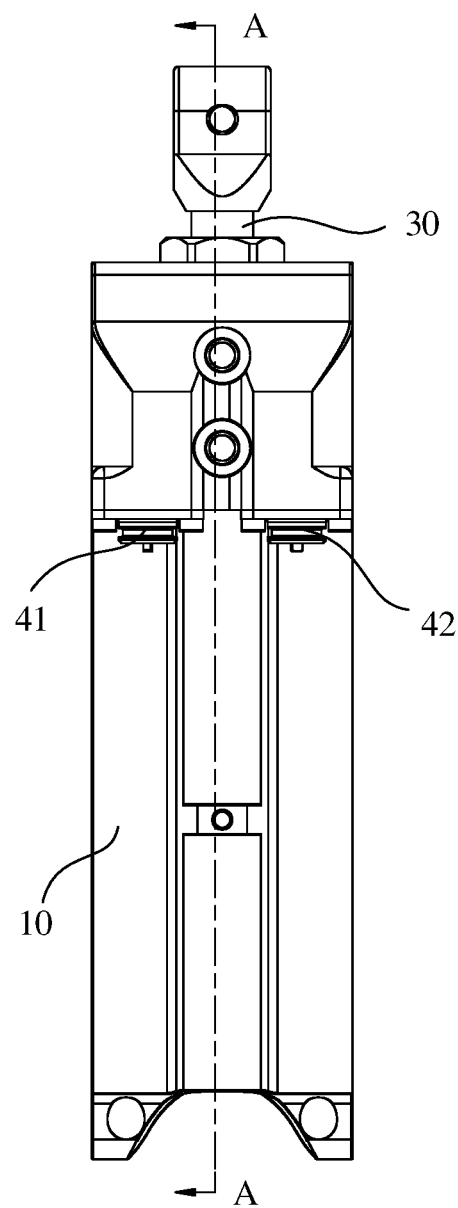
FIG. 2 is a planar view of the hydraulic damper in the embodiment of FIG. 1.

Providing a clear and complete description for the technical solutions in the embodiments of the present disclosure in combination with the accompanying drawings in the embodiments of the present disclosure. Obviously, the embodiments described herein are only a part of the embodiments of the present disclosure, not all of them. Based on the embodiments in the present disclosure, all other embodiments obtained by those skilled in the art without creative work fall within the protection scope of the present disclosure.

It should be noted that all directional indications (such as top, bottom, left, right, front, rear . . . ) in the embodiments of the present disclosure are only used to explain the relative position relationship, motion situation, etc. between components in a specific position (as shown in the accompanying figures). If the specific position changes, the directional indication also changes accordingly.

It should also be noted that when a component is referred to as "fixed to" or "set to" another component, the component may be directly on the another component or there may be a centering component at the same time. When a component is referred to as "connected to" another component, the component may be directly connected to the another component or there may be a centering component at the same time.

In addition, the descriptions of "first", "second", etc. in the present disclosure is only used for descriptive purposes, and cannot be understood as indicating or implying their relative importance or implying the number of indicated technical features. Therefore, features limited to "first" and "second" can explicitly or implicitly include at least one of the features. In addition, technical solutions between various embodiments can be combined with each other, but must be based on what those ordinary skilled in the art can achieve. When a combination of technical solutions conflicts or cannot be achieved, it should be considered that the combination of the technical solutions does not exist and is not within the protection scope required by the present disclosure.

The present disclosure provides a hydraulic damper mainly applied to various prosthetic products.

Referring to FIGS. 1-4, in this embodiment, the hydraulic damper comprises a housing 10, a piston 20, a piston rod 30, and a damping adjustment component 40 (unmarked). Wherein:

The housing 10 has an energy storage chamber 12 and a damping chamber 11 therein which are loaded with hydraulic fluid. The damping chamber 11 and the energy storage chamber 12 are two independent cavities. The hydraulic fluid may be hydraulic oil or hydraulic fluid with similar functions to the hydraulic oil. In the following description, the hydraulic oil is taken as an example;

The piston 20 is movably arranged inside the damping chamber 11, and the piston 20 separates the damping chamber 11 into a first chamber 111 and a second chamber 112. The energy storage chamber 12 is closer to the second chamber 112, and a dynamic seal is adopted between the piston 20 and an internal circumferential wall of the damping chamber 11;

The piston rod 30 is inserted into the first chamber 111, and one end of the piston rod 30 is connected to the piston 20, another end of the piston rod 30 penetrates through one end of the housing 10 away from the energy storage chamber 12. The piston rod 30 is configured to drive the piston 20 to move back and forth in the damping chamber 11 to dynamically adjust a volume of the first chamber 111 and a volume of the second chamber 112;

The damping adjustment component 40 is connected to and communicates with the first chamber 111, the second chamber 112, and the energy storage chamber 12 to adjust a resistance of a movement of the piston 20. The damping adjustment component 40 can be arranged inside or outside the housing 10; and some components of the damping adjustment component 40 can be arranged outside the housing 10, while the other components thereof can be arranged inside the housing 10.

A principle of the hydraulic damper in the present embodiment in use is as follows: human load acts on the end of the piston rod 30 penetrating through the housing 10. When the human load presses the piston rod 30 toward inward the housing 10, the piston rod 30 drives the piston 20 to move toward the second chamber 112. The hydraulic oil in the second chamber 112 flows into the energy storage chamber 12 through the damping adjustment component 40, and the hydraulic oil in the energy storage chamber 12 flows into the first chamber 111 through the damping adjustment component 40. By adjusting the damping adjustment component 40 to change an opening size of the hydraulic oil flowing out of the second chamber 112, a corresponding pressure can be established in the second chamber 112 to prevent the piston 20 from moving toward the second chamber 112, thus obtaining a desired resistance (i.e. buffering force). When the human load is removed, a pressure of the first chamber 111 and that of the second chamber 112 are actually the same; however, due to the fact that an action area of the hydraulic oil in the second chamber 112 on the piston 20 is greater than that of the hydraulic oil in the first chamber 111 on the piston the hydraulic oil in the second chamber 112 generates a propulsive force on the piston 20 toward the first chamber 111; the propulsive oil in the first chamber 111 enters the energy storage chamber 12 through the damping adjustment component 40; the hydraulic oil in the energy storage chamber 12 enters the second chamber 112 through the damping adjustment component 40; the piston 20 drives the piston rod 30 to automatically move outward. At this time, an opening size of the hydraulic oil of the first chamber 111 can also be changed by adjusting the damping adjustment component so as to adjust a buffering force of the piston 20 driving the piston rod 30 to move outward.

In the hydraulic damper of the present embodiment, the energy storage chamber 12 is arranged closer to the second chamber 112, i.e. the energy storage chamber 12 is arranged at the end of the housing 10 away from the piston rod 30, so that the piston rod 30 no longer needs to pass through the energy storage chamber 12 and can penetrate through the housing 10, thereby eliminating a dynamic sealing treatment between the piston rod 30 and the energy storage chamber 12, reducing an overall sealing difficulty of the hydraulic damper, and reducing production costs, and moreover saving a length of one segment of the piston rod 30 passing through the energy storage chamber 12, reducing a length of the piston rod 30, and reducing a weight of the piston rod, thereby reducing an overall weight of the hydraulic damper, and making a weight of the prosthetics using the hydraulic damper lighter and more portable, thus reducing the burden on the user.

In the present embodiment, the energy storage chamber 12, the second chamber 112, and the first chamber 111 are sequentially distributed along an axial direction of the piston 20 for facilitating a design of a liquid passage between each chamber, reducing a radial size of the hydraulic damper, and making an overall appearance of the hydraulic damper more compact. Certainly, in other embodiments, the energy storage chamber 12 may also be arranged at one side of the second chamber 112, or arranged around the second chamber 112, etc.

Figure 4:
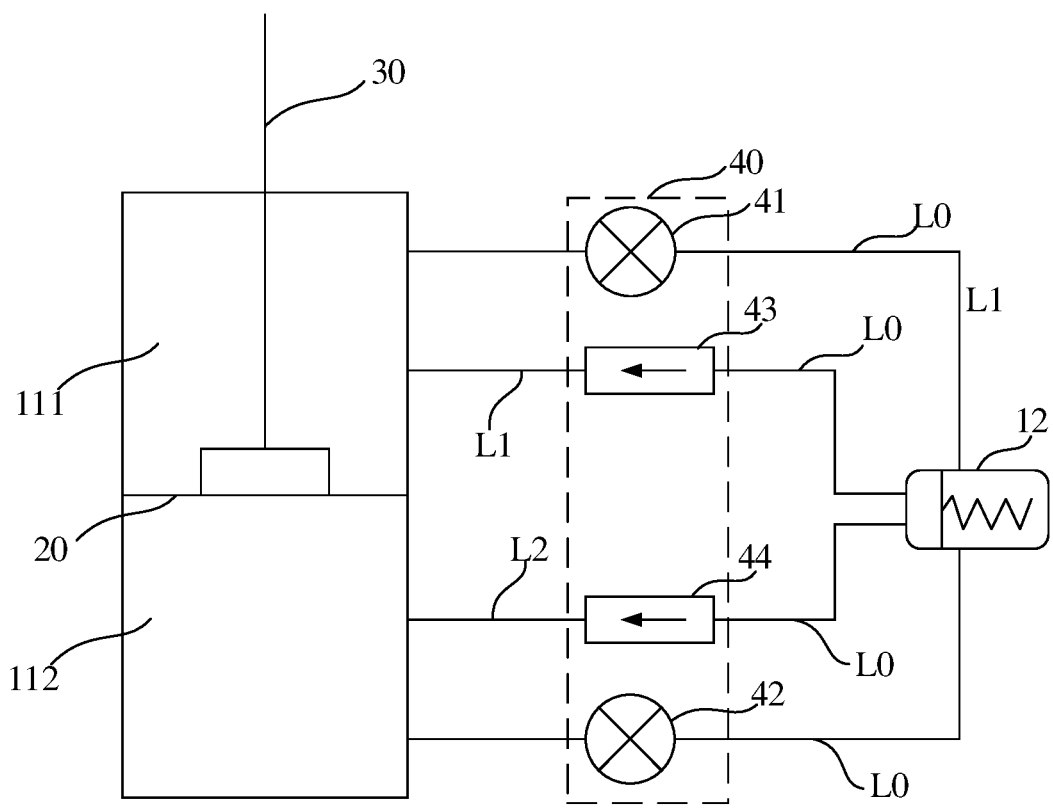
FIG. 4 is a schematic diagram of a structure of a flow path of a hydraulic system of a hydraulic damper in one embodiment of the present disclosure.

Referring to FIG. 4, in this embodiment, the damping adjustment component 40 comprises a first throttle valve 41, a second throttle valve 42, a first non-return valve 43, and a second non-return valve 44. One end of the first throttle valve 41 is connected to and communicates with the first chamber 111, and another end is connected to and communicates with the energy storage chamber 12. One end of the second throttle valve 42 is connected to and communicates with the second chamber 112, and another end is connected to and communicates with the energy storage chamber 12. The energy storage chamber 12 is connected to and communicates with the first chamber 111 through the first non-return valve 43, and the energy storage chamber 12 is connected to and communicates with the second chamber 112 through the second non-return valve 44, that is, that is, the first non-return valve 43 only flows in a direction of the energy storage chamber 12 toward the first chamber 111, and the second non-return valve 44 only flows in a direction of the energy storage chamber 12 toward the second chamber 112.

In the present embodiment, a working principle of the damping adjustment component 40 to achieve damping adjustment is as follows: when the human load presses the piston rod 30 toward inward the housing 10, the piston rod 30 drives the piston 20 to move toward the second chamber 112; at this time, the first throttle valve 41 closes, the second throttle valve 42 opens, the hydraulic oil in the second chamber 112 flows into the energy storage chamber 12 through the second throttle valve 42, while the hydraulic oil in the energy storage chamber 12 flows into the first chamber 111 through the first non-return valve 43. By adjusting the opening size of the second throttle valve 42, a speed of the hydraulic oil flowing out of the second chamber 112 through the second throttle valve 42 can be changed, that is, a resistance (i.e. buffering force) of the hydraulic oil in the second chamber 112 that prevents the piston 20 from moving toward the second chamber 112 can be changed. After the human body load is removed, the hydraulic oil in the second chamber 112 generates a propulsive force on the piston 20 toward the first chamber 111; at this time, the first throttle valve 41 opens, the second throttle valve 42 closes, the hydraulic oil in the first chamber 111 flows into the energy storage chamber 12 through the first throttle valve 41, the hydraulic oil in the energy storage chamber 12 flows into the second chamber 112 through the second non-return valve 44, and the piston 20 drives the piston rod 30 to automatically move outward. During this process, By adjusting the opening size of the first throttle valve 41, a speed of the hydraulic oil flowing out of the first chamber 111 can be adjusted, that is, a resistance of the hydraulic oil in the first chamber 111 that prevents the piston from driving the piston rod 30 to move outward can be adjusted.

Figure 3:
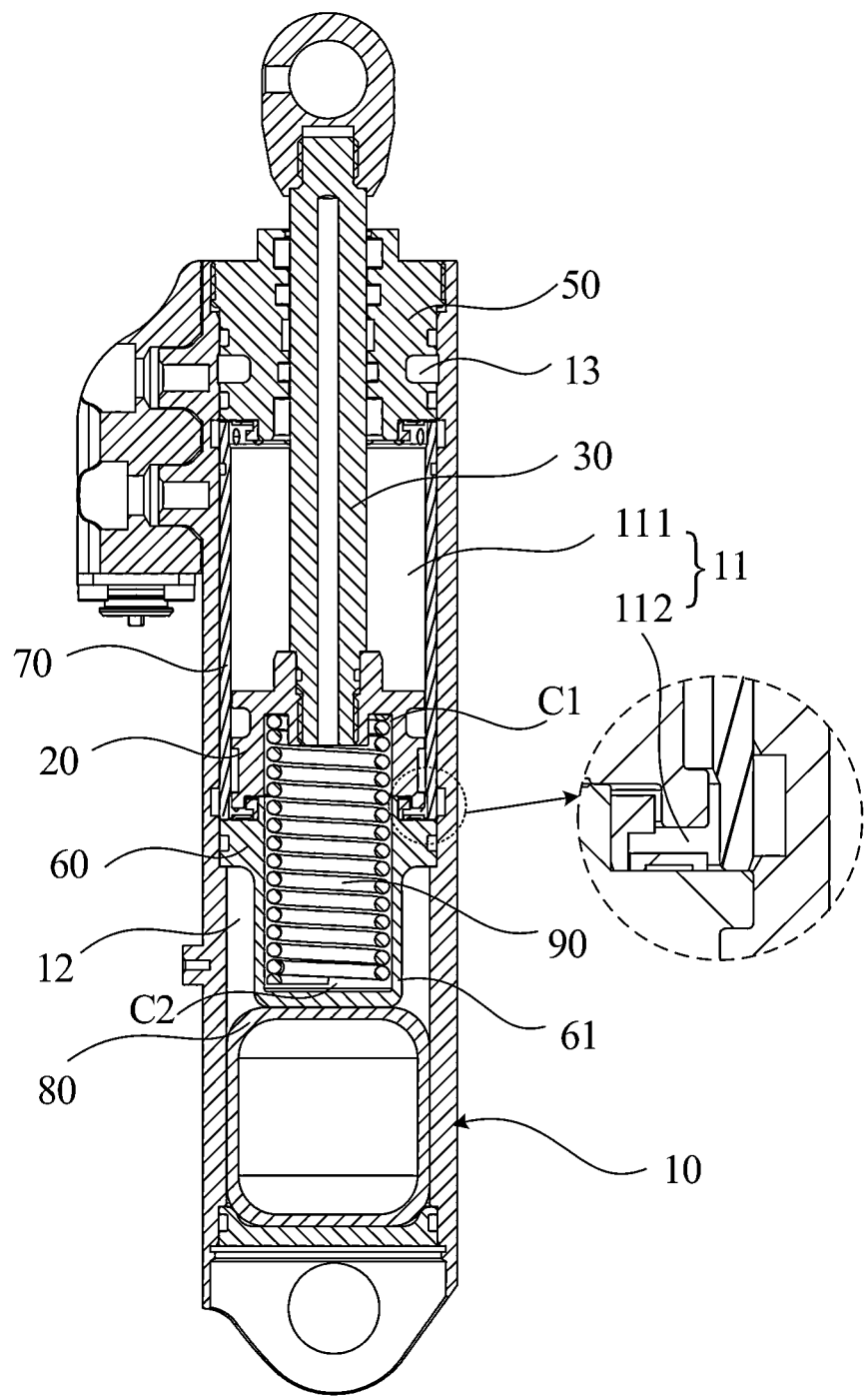
FIG. 3 is a cross-sectional schematic diagram of an A-A direction in FIG. 2, with a local enlarged view.
Figure 5:
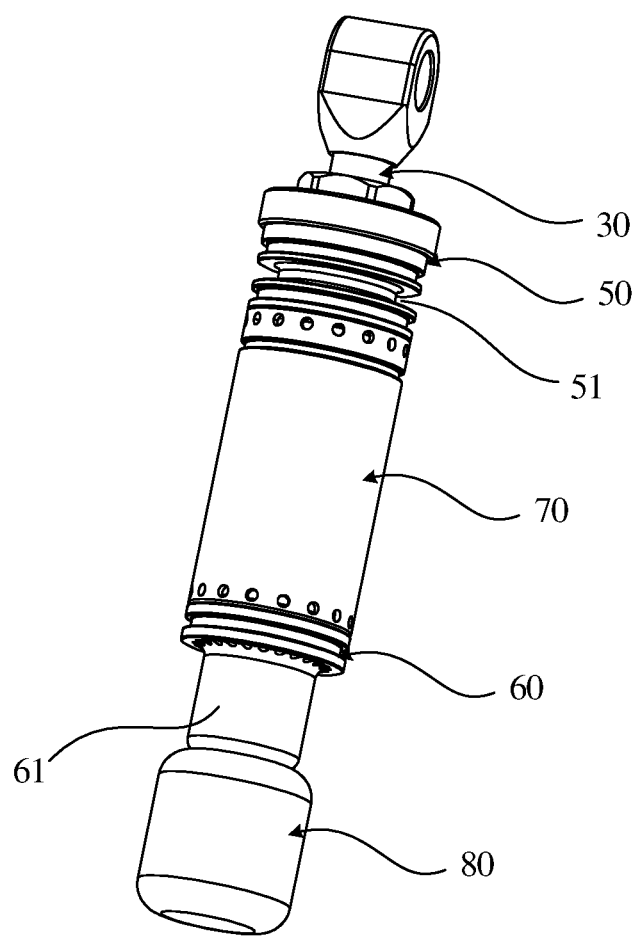
FIG. 5 is a schematic diagram of a partial structure of a hydraulic damper in one embodiment of the present disclosure.
Figure 6:
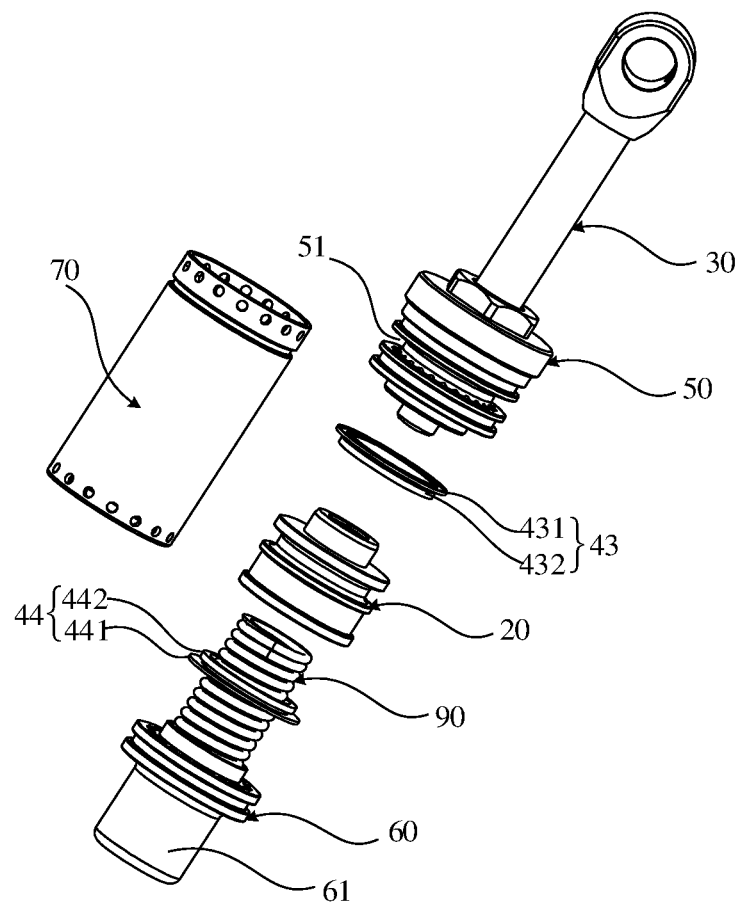
FIG. 6 is an exploded schematic diagram of the partial structure in the embodiment of FIG. 5.
Figure 7:
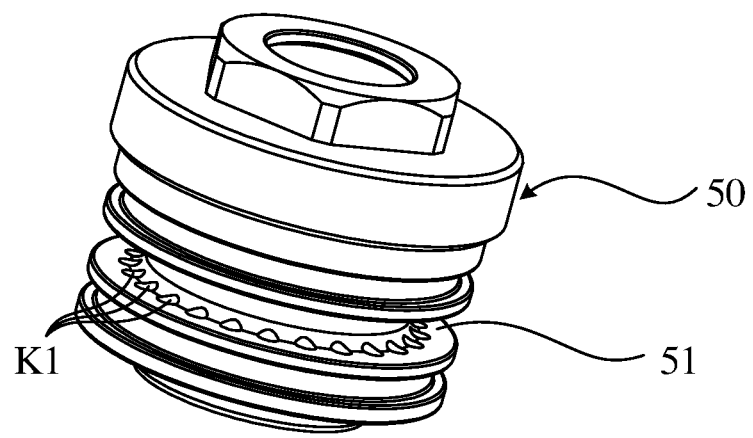
FIG. 7 is a schematic diagram of a structure of a first cylinder head in the embodiment of FIG. 5.

Referring to FIGS. 3, 5, and 6, in this embodiment, the hydraulic damper further comprises a first cylinder head 50 and a second cylinder head 60 both arranged in the housing 10. A damping chamber 11 is formed between the first cylinder head 50 and the second cylinder head 60. The first cylinder head 50 is closer to the first chamber 111 and the second cylinder head 60 is closer to the second chamber 112. Among them, the first cylinder head 50 and the second cylinder head 60 are respectively sealed and fitted with an internal circumferential wall of the housing 10, and there is a dynamic seal between the first cylinder head 50 and the piston rod 30. In the present embodiment, the housing 10 is further arranged with a cylinder barrel 70 therein. The first cylinder head 50 and the second cylinder head 60 are respectively sealed at both ends of the cylinder barrel 70 and cover the cylinder barrel 70, thereby enclosing and forming the damping chamber 11. Certainly, in other embodiments, the cylinder barrel 70 may not be required; the first cylinder head 50 and the second cylinder head 60 are directly enclosed with the internal circumferential wall of the housing 10 to form the damping chamber 11.

Among them, a liquid passage L0 is arranged inside a side wall of the housing which is used as a passage for the hydraulic oil. Arranging the liquid passage L0 inside the side wall of the housing 10, avoids the damage risk caused by exposure of the liquid passage L0 and ensures stability and reliability of the liquid passage L0.

Referring to FIGS. 3-8, an external circumferential wall of the first cylinder head 50 is provided with a slot 51 (taking an annular groove as an example in the figures) that encloses with an inner wall of the housing 10 to form a transit chamber 13. The first cylinder head 50 is provided with a first passage L1 thereon, and the first passage L1 is connected to and communicated with the first chamber 111 and the transit chamber 13. The first non-return valve 43 is set at one end of the first passage L1. The transit chamber 13 is connected to and communicated with the energy storage chamber 12 through the liquid passage L0. The second cylinder head 60 is provided with a second passage L2 thereon, and the second passage L2 is connected to and communicated with the second chamber 112 and the energy storage chamber 12. The second non-return valve 44 is set at one end of the second passage L2. In this embodiment, taking a plurality of first passing holes K1 uniformly distributed around an axis of the piston rod 30 as an example for the first passage L1, and taking a plurality of second passing holes K2 uniformly distributed around the axis of the piston rod 30 as an example for the second passage L2; certainly, in other embodiments, the first passage L1 and the second passage L2 may also be other structures, such as an annular through groove. In the present embodiment, the first non-return valve 43 comprises a first annular elastic sheet 431 and a first limiting member 432 that limits the first annular elastic sheet 431 and prevents detachment of the first annular elastic sheet 431. The first annular elastic sheet 431 seals and covers each first passing hole K1, and one side of the first annular elastic sheet 431 toward the first passing hole K1 is arranged with an annular groove coaxial with the first annular elastic sheet 431. The second non-return valve 44 comprises a second annular elastic sheet 441 and a second limiting member 442 that limits the second annular elastic sheet 441 and prevents detachment of the second annular elastic sheet 441. The second annular elastic sheet 441 seals and covers each second passing hole K2, and one side of the second annular elastic sheet 441 toward the second passing hole K2 is arranged with an annular groove coaxial with the second annular elastic sheet 441.

Among them, the first throttle valve 41 and the second throttle valve 42 are both arranged on an outer wall of the housing 10. Two ends of the first throttle valve 41 are respectively connected to and communicated with the first chamber 111 and the energy storage chamber 12 correspondingly through the liquid passage L0, and two ends of the second throttle valve 42 are respectively connected to and communicated with the second chamber 112 and the energy storage chamber 12 correspondingly through the liquid passage L0; that is, one end of the first throttle valve 41 is connected to and communicated with the first chamber 111 through the liquid passage L0, another end of the first throttle valve 41 is connected to and communicated with the energy storage chamber 12 through the liquid passage L0, and one end of the second throttle valve 42 is connected to and communicated with the second chamber 112 through the liquid passage L0, and another end of the second throttle valve 42 is connected to and communicated with the energy storage chamber 12 through the liquid passage L0.

In the present embodiment, a connection-and-communication method between the first chamber 111, the second chamber 112, the transit chamber 13, and the energy storage chamber 12 with the liquid passage L0 may be by opening a connection-and-communication portion (such as a through hole, a through groove, or a connecting pipe) connected with the liquid passage L0 on a side wall of the first chamber 111, the second chamber 112, the transit chamber 13, and/or the energy storage chamber 12.

Referring to FIGS. 3, 5, and 6, in this embodiment, an elastomer 80 with a sealed chamber inside is arranged inside the energy storage chamber 12. The elastomer 80 may be a hollow elastic ball (spherical or ellipsoidal), a hollow elastic column (circular or square), a hollow ring, and etc. made from elastic materials (such as rubber or other polymers) or other similar materials. In figures of the present embodiment, only a circular hollow elastic column is used as an example, structures and shapes of the elastomer 80 are not limited here. By setting the elastomer 80 inside the energy storage chamber 12, when the hydraulic oil flows into the energy storage chamber 12, a surface pressure of the elastomer 80 is greater than an air pressure in the sealed chamber thereof. The hydraulic oil in the energy storage chamber 12 squeezes the elastomer 80, causing the elastomer 80 to gradually compress air in the sealed chamber for energy accumulating. When the hydraulic oil flows out of the energy storage chamber 12, the surface pressure of the elastomer 80 is less than the air pressure in the sealed chamber thereof. The air in the sealed chamber of the elastomer 80 gradually expands, releasing energy outward, then the elastomer 80 gradually returns to its initial state. Certainly, the present embodiment only takes the scheme of setting the above-mentioned elastomer 80 inside the energy storage chamber 12 as an example, and in other embodiments, the energy storage chamber 12 may also be arranged with other energy-accumulating devices therein (such as a spring).

Furthermore, one end of the elastomer 80 abuts against one end of the energy storage chamber 12 away from the second chamber 112, and an external circumferential wall of the elastomer 80 and an internal circumferential wall of the energy storage chamber 12 are sealed and fitted together, that is, the elastomer 80 is clamped in one segment of the energy storage chamber 12 away from the second chamber 112. This embodiment ensures that the hydraulic oil inside one segment of the energy storage chamber 12 closer to the second chamber 112 does not leak out from the end of the energy storage chamber 12 away from the second chamber 112 by arranging the external circumferential wall of the elastomer 80 sealed with and fitted on the internal circumferential wall of the energy storage chamber 12, that is, the elastomer 80 achieves sealing the end of the energy storage chamber 12 away from the second chamber 112. Therefore, the end of the energy storage chamber 12 away from the second chamber 112 does not need to be sealed with sealing members, simplifying a sealing design for hydraulic dampers, further reducing an overall sealing difficulty of hydraulic dampers.

Furthermore, a chamber wall of the energy storage chamber 12 closer to the second chamber 112 is arranged with a supporting part 61 protrudingly toward the elastomer 80. The supporting part 61 is connected to and abuts against the elastomer 80, that is, the elastomer 80 is limited between the end of the energy storage chamber 12 away from the second chamber 112 and the supporting part 61, such that the elastomer 80 can be prevented from moving in the energy storage chamber 12, ensuring the a sealing and fitting effect between the external circumferential wall of the elastomer 80 and the internal circumferential wall of the energy storage chamber 12, i.e. ensuring a sealing performance of the energy storage chamber 12. Among them, the supporting part 61 may be formed by a protrusion of the second cylinder head 60 toward the elastomer 80.

Referring to FIG. 3 and FIG. 6, in this embodiment, the hydraulic damper further comprises an elastic device 90 arranged in the second chamber 112, the elastic device 90 acts elastically on the piston 20 and applies a force on the piston 20 toward the first chamber 111. The hydraulic damper of the present embodiment has the elastic device 90 added in the second chamber 112, so that when the human load presses the piston rod 30 into the housing 10, the force of the elastic device 90 forms a partial buffering force that prevents the piston 20 from moving to the second chamber 112, and the partial buffering force gradually increases with the distance of the piston rod 30 moving toward the second chamber 112 increases. When the human load on the piston rod 30 is removed, the force of the elastic device 90 on the piston 20 forms a partial propulsive force that propels the piston 20 to move toward the first chamber 111, and the partial propulsive force gradually decreases as the distance of the piston rod 30 moving toward the first chamber 111 increases.

In the present embodiment, adopting the elastic force of the elastic device 90 to replace the hydraulic pressure effect of partial hydraulic oil, thereby a resistance in the hydraulic damper is changed to consist of two parts, the elastic force of the elastic device 90 and the hydraulic pressure, so that the system hydraulic pressure of the hydraulic damper can be reduced (for example, it can be reduced from the original system hydraulic pressure of around 1.5 MPa to the system hydraulic pressure of around 0.4 Mpa). The decrease in system hydraulic pressure greatly reduces the sealing requirements of various parts in the hydraulic damper, further reducing the sealing difficulty of the hydraulic damper and reducing production costs. In addition, due to the fact that a large part of the resistance of the hydraulic damper is provided by the elastic force of the elastic device 90, even if hydraulic oil leakage occurs due to unexpected circumstances, the impact on the damping performance of the hydraulic damper is relatively small, which can ensure that the hydraulic damper can continue to be used normally and avoid the situation where the hydraulic damper loses efficiency directly due to oil leakage and thereby leading to paralysis of prosthetic products.

Figure 8:
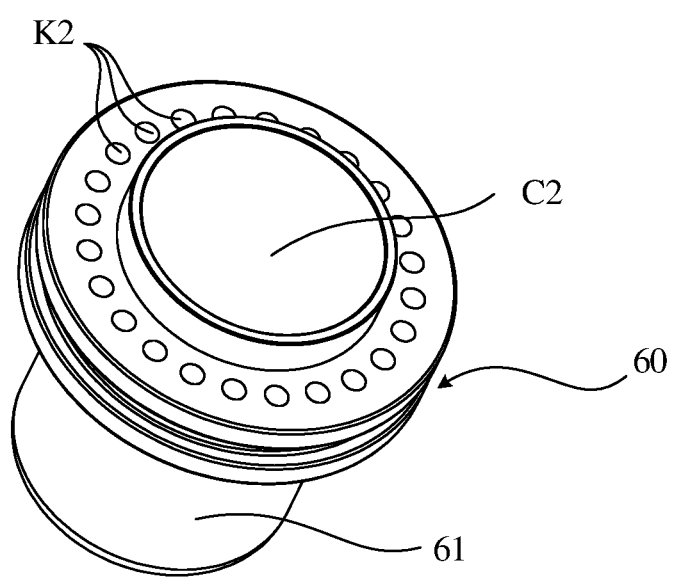
FIG. 8 is a schematic diagram of a structure of a second cylinder head in the embodiment of FIG. 5.

Referring to FIG. 3, FIG. 5, and FIG. 8, in some embodiments, the elastic device 90 comprises a retractable spring. One end of the piston 20 facing the second chamber 112 is concavely arranged with a first locating slot C1, and one end of the retractable spring is inserted into the first locating slot C1 and elastically abuts against a bottom of the first locating slot. One chamber wall of the second chamber 112 closer to energy storage chamber 12 is concavely arranged with a second locating slot C2, and another end of the retractable spring is inserted into the second locating slot C2 and elastically abuts against a bottom of the second locating slot. By inserting both ends of the retractable spring into the first locating slot C1 and the second locating slot C2, the first locating slot C1 and the second locating slot C2 may be designed to fit a shape and size of the retractable spring, so as to ensure that the location of the retractable spring is stable and does not cause displacement during use, which affects the elastic performance. Among them, the second locating slot C2 may be constructed on the second cylinder head 60 mentioned above, and the second locating slot C2 may be constructed on one side of the supporting part deviating from the elastomer 80.

It should be noted that the present embodiment only takes the scheme where the elastic device 90 comprises the retractable spring as an example. Certainly, in other embodiments, the elastic device 90 may also comprise other structural components, or the elastic device 90 may adopt other structural schemes instead of the retractable spring. For example, the elastic device 90 comprises elastic rubber blocks, elastic sheets, or other component structures.

The present disclosure further provides an intelligent prosthetics, which comprises the hydraulic damper mentioned above. The specific structure of the hydraulic damper refers to the above embodiments. As the intelligent prosthetics adopts all the technical solutions of all the above embodiments of hydraulic damper, it has at least all the beneficial effects brought by the technical solutions of the above embodiments, and does not to be repeated here.

In some embodiments, the intelligent prosthetics can collect, analyze, and process myoelectricity signals of the surface of the user's installation part (such as the thigh), and combine them with preinstalled physical sensors, so as to identify the user's intention and the current state of the intelligent prosthetics to control the joints to perform corresponding movements.

These above are only partial or preferred embodiments of the present disclosure, and neither the text nor the accompanying drawings can therefore limit the protection scope of the present disclosure. Under the overall conception of the present disclosure, any equivalent structural transformations or direct/indirect applications applied to other related technical fields, made by using the content of the specification and accompanying drawings of the present disclosure, are included in the protection scope of the present disclosure.

What is claimed is:

1. A hydraulic damper, applied to a prosthetics, comprising:
   a housing;
   an energy storage chamber and a damping chamber, both loaded with a hydraulic fluid, arranged inside the housing;
   a piston movably arranged inside the damping chamber, separating the damping chamber into a first chamber and a second chamber, wherein a movement of the piston adjusts a volume of the first chamber and a volume of the second chamber, and wherein the energy storage chamber is closer to the second chamber than to the first chamber;
   a piston rod inserted into the first chamber, wherein one end of the piston rod is connected to the piston, and another end of the piston rod penetrates through one end of the housing away from the energy storage chamber; and
   a damping adjustment component connected to the first chamber, the second chamber, and the energy storage chamber respectively, and configured to adjust a resistance of a movement of the piston.

2. The hydraulic damper according to claim 1, wherein the energy storage chamber, the second chamber, and the first chamber are sequentially distributed along an axial direction of the piston.

3. The hydraulic damper according to claim 1, wherein the damping adjustment component comprises:
   a first throttle valve, one end of the first throttle valve being connected to the first chamber, and another end of the first throttle valve being connected to the energy storage chamber;
   a second throttle valve, one end of the second throttle valve being connected to the second chamber, and another end of the second throttle valve being connected to the energy storage chamber;

a first non-return valve, through which the first non-return valve the energy storage chamber is connected to the first chamber; and a second non-return valve, through which the second non-return valve the energy storage chamber is connected to the second chamber.

4. The hydraulic damper according to claim 3, further comprising:

a first cylinder head and a second cylinder head arranged inside the housing, wherein:

the damping chamber is formed between the first cylinder head and the second cylinder head, the first cylinder head is closer to the first chamber, and the second cylinder head is closer to the second chamber;

a liquid passage is arranged inside a side wall of the housing;

an external circumferential wall of the first cylinder head is arranged with a slot that encloses with an inner wall of the housing to form a transit chamber, a first passage is arranged on the first cylinder head to be connected to both the first chamber and the transit chamber, the first non-return valve is arranged at one end of the first passage, and the transit chamber is connected to the energy storage chamber through the liquid passage;

a second passage is arranged on the second cylinder head to be connected to both the second chamber and the energy storage chamber, and the second non-return valve is arranged at one end of the second chamber; and the first throttle valve and the second throttle valve are arranged on an outer wall of the housing, two ends of the first throttle valve are respectively connected to the first chamber and the energy storage chamber correspondingly through the liquid passage, and two ends of the second throttle valve are respectively connected to the second chamber and the energy storage chamber correspondingly through the liquid passage.

5. The hydraulic damper according to claim 1, wherein an elastomer with a sealed chamber inside is arranged inside the energy storage chamber.

6. The hydraulic damper according to claim 5, wherein one end of the elastomer abuts against one end of the energy storage chamber away from the second chamber, and an external circumferential wall of the elastomer and an internal circumferential wall of the energy storage chamber are sealed and fitted together.

7. The hydraulic damper according to claim 6, wherein one chamber wall of the energy storage chamber closer to the second chamber is arranged with a supporting part protruding toward the elastomer, and the supporting part abuts against the elastomer.

8. The hydraulic damper according to claim 1, further comprising an elastic device arranged in the second chamber, wherein the elastic device acts elastically on the piston and applies a force on the piston toward the first chamber.

9. The hydraulic damper according to claim 8, wherein:

the elastic device comprises a retractable spring, one end of the piston facing the second chamber is concavely arranged with a first locating slot, one end of the retractable spring is inserted into the first locating slot and elastically abuts against a bottom of the first locating slot; and one chamber wall of the second chamber closer to the energy storage chamber is concavely arranged with a second locating slot, and another end of the retractable spring is inserted into the second locating slot and elastically abuts against a bottom of the second locating slot.

10. An intelligent prosthetics, comprising a hydraulic damper, the hydraulic damper comprising:

a housing, an energy storage chamber and a damping chamber, both loaded with a hydraulic fluid, arranged inside the housing;

a piston movably arranged inside the damping chamber, separating the damping chamber into a first chamber and a second chamber, wherein a movement of the piston adjusts a volume of the first chamber and a volume of the second chamber, and wherein the energy storage chamber is closer to the second chamber than to the first chamber;

a piston rod inserted into the first chamber, wherein one end of the piston rod is connected to the piston, and another end of the piston rod penetrates through one end of the housing away from the energy storage chamber; and a damping adjustment component connected to the first chamber, the second chamber, and the energy storage chamber, respectively, and configured to adjust a resistance of a movement of the piston.

11. The intelligent prosthetics according to claim 10, wherein the energy storage chamber, the second chamber, and the first chamber are sequentially distributed along an axial direction of the piston.

12. The intelligent prosthetics according to claim 10, wherein the damping adjustment component comprises:

a first throttle valve, one end of the first throttle valve being connected to the first chamber, and another end of the first throttle valve being connected to the energy storage chamber;

a second throttle valve, one end of the second throttle valve being connected to the second chamber, and another end of the second throttle valve being connected to the energy storage chamber;

a first non-return valve, through which the first non-return valve the energy storage chamber is connected to the first chamber; and a second non-return valve, through which the second non-return valve the energy storage chamber is connected to the second chamber.

13. The intelligent prosthetics according to claim 12, wherein:

the hydraulic damper further comprises a first cylinder head and a second cylinder head arranged inside the housing, the damping chamber is formed between the first cylinder head and the second cylinder head, the first cylinder head is closer to the first chamber, and the second cylinder head is closer to the second chamber;

a liquid passage is arranged inside a side wall of the housing;

an external circumferential wall of the first cylinder head is arranged with a slot that encloses with an inner wall of the housing to form a transit chamber, a first passage is arranged on the first cylinder head to be connected to both the first chamber and the transit chamber, the first non-return valve is arranged at one end of the first passage, and the transit chamber is connected to the energy storage chamber through the liquid passage;

a second passage is arranged on the second cylinder head to be connected to both the second chamber and the energy storage chamber, and the second non-return valve is arranged at one end of the second chamber; and the first throttle valve and the second throttle valve are arranged on an outer wall of the housing, two ends of the first throttle valve are respectively connected to the first chamber and the energy storage chamber correspondingly through the liquid passage, and two ends of the second throttle valve are respectively connected to the second chamber and the energy storage chamber correspondingly through the liquid passage.

14. The intelligent prosthetics according to claim 10, wherein an elastomer with a sealed chamber inside is arranged inside the energy storage chamber.

15. The intelligent prosthetics according to claim 14, wherein one end of the elastomer abuts against one end of the energy storage chamber away from the second chamber, and an external circumferential wall of the elastomer and an internal circumferential wall of the energy storage chamber are sealed and fitted together.

16. The intelligent prosthetics according to claim 15, wherein one chamber wall of the energy storage chamber closer to the second chamber is arranged with a supporting part protruding toward the elastomer, and the supporting part abuts against the elastomer.

17. The intelligent prosthetics according to claim 10, wherein the hydraulic damper further comprises an elastic device arranged in the second chamber, wherein the elastic device acts elastically on the piston and applies a force on the piston toward the first chamber.

18. The intelligent prosthetics according to claim 17, wherein:
- the elastic device comprises a retractable spring, one end of the piston facing the second chamber is concavely arranged with a first locating slot, one end of the retractable spring is inserted into the first locating slot and elastically abuts against a bottom of the first locating slot; and
- one chamber wall of the second chamber closer to the energy storage chamber is concavely arranged with a second locating slot, and another end of the retractable spring is inserted into the second locating slot and elastically abuts against a bottom of the second locating slot.

* * * * *